US00PP29776P2

(12) United States Plant Patent
Bacon

(10) Patent No.: US PP29,776 P2
(45) Date of Patent: Oct. 30, 2018

(54) PLUM TREE NAMED 'SUPLUMFIFTYTWO'

(50) Latin Name: *Prunus salicina*
Varietal Denomination: Suplumfiftytwo

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 15/732,683

(22) Filed: Dec. 14, 2017

(51) Int. Cl.
*A01H 5/08* (2018.01)

(52) U.S. Cl.
USPC ..... Plt./184
CPC ..... *A01H 5/0862* (2013.01)

(58) Field of Classification Search
USPC ..... Plt./184
See application file for complete search history.

*Primary Examiner* — Kent L Bell
(74) *Attorney, Agent, or Firm* — Knobbe, Martens, Olson & Bear, LLP

(57) ABSTRACT

A new and distinct plum tree variety, *Prunus salicina*, cv. 'Suplumfiftytwo' is characterized by having large fruit with dark red flesh. The fruit of the new variety 'Suplumfiftytwo' is also moderately firm, juicy and has a mild sweet flavor. The date of the harvest of the fruit of the new variety is later than for 'Black Splendor' (unpatented) and 'Flavorosa' (U.S. Plant Pat. No. 10,285). The fruit of the new variety 'Suplumfiftytwo' is larger than the fruit of 'Black Splendor' (unpatented) and 'Flavorosa' (U.S. Plant Pat. No. 10,285).

1 Drawing Sheet

Latin name of the genus and species claimed: *Prunus salicina.*

Variety denomination: 'Suplumfiftytwo'.

BACKGROUND AND SUMMARY OF THE INVENTION

This invention relates to the discovery and asexual propagation of a new and distinct variety of plum, *Prunus salicina* cv. 'Suplumfiftytwo'. The new variety was first originated by hybridization in June 2015 by Terry A. Bacon as breeder number 'PL1748RB'.

The new variety 'Suplumfiftytwo' is characterized by having large fruit with dark red flesh. The fruit of the new variety 'Suplumfiftytwo' is also moderately firm, juicy and has a mild sweet flavor.

The seed parent is 'PL608YB' (unpatented breeding selection), and the pollen parent 'PL374RR' (unpatented breeding selection). The parent varieties were first crossed in February 2012, with the date of first sowing being February 2013, and the date of first flowering being February 2015. The new variety 'Suplumfiftytwo' was first asexually propagated by Terry Bacon near Wasco, Kern County, Calif. in February 2016 by dormant grafting.

The new variety 'Suplumfiftytwo' is similar to its pollen parent 'PL374RR' in that the fruit of both varieties has red flesh. The new variety 'Suplumfiftytwo' differs from 'PL374RR' in that the ripening of the fruit of the new variety starts 29 days later and the size of the fruit of the new variety 'Suplumfiftytwo' is larger, at 68 mm compared to 58 mm for 'PL374RR'.

The new variety 'Suplumfiftytwo' is differs from its seed parent 'PL608YB' in that the fruit of the new variety has red flesh while the fruit of 'PL608YB' has yellow flesh.

The fruit of the new variety 'Suplumfiftytwo' ripens at about the same time as the fruit of 'Black Splendor' (unpatented) and the fruit of both varieties has red flesh. The new variety 'Suplumfiftytwo' differs from 'Black Splendor' in that the new variety has a larger fruit size at about 68 mm compared to 64 mm for 'Black Splendor'. In addition, the new variety 'Suplumfiftytwo' has a brix of 17 degrees and a brix:acid ratio of 34, while 'Black Splendor' has a brix of 14 degrees and brix:acid ratio of 26. The fruit of the new variety 'Suplumfiftytwo' has a red flesh like the fruit of 'Flavorosa' (U.S. Plant Pat. No. 10,285), but the ripening of the fruit of the new variety 'Suplumfiftytwo' starts about 18 days later than that of 'Flavorosa' (U.S. Plant Pat. No. 10,285) The new variety 'Suplumfiftytwo' also has a larger fruit size at 68 mm compared to 56 mm for 'Flavorosa'.

The new variety 'Suplumfiftytwo' has been shown to maintain its distinguishing characteristics through successive asexual propagations by, for example, cuttings and grafting.

BRIEF DESCRIPTION OF THE PHOTOGRAPH

The accompanying color photographic illustration FIG. 1 shows typical specimens of the foliage and fruit of the present new plum variety 'Suplumfiftytwo'. The illustration shows the upper and lower surface of the leaves, a view of the fruit as a whole, the stone as a whole, and a sectional view of a fruit divided across its suture plane to show flesh color, pit cavity and the stone remaining in place. The photographic illustration was taken shortly after being picked and the colors are as nearly true as is reasonably possible in a color representation of this type. The photographs depict fruit and vegetative growth from a four year old tree.

DETAILED DESCRIPTION OF THE PREFERRED EMBODIMENT

Throughout this specification color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to four year old 'Suplumfiftytwo' plants grown in the vicinity of Wasco, Kern County, Calif., during 2017 and is believed to apply to plants of the variety grown under similar conditions of soil and climate elsewhere.

TREE

General: (Measurements taken on four year old trees unless otherwise noted).

- *Size*.—Medium, reaches a height of approximately 3 meters with normal pruning.
- *Habit*.—Spreading.
- *Vigor*.—Medium; top shoot growth of at least 1 meter during the growing season.
- *Productivity*.—Very Productive.
- *Bearer*.—On spurs and long shoots.
- *Fertility*.—Self-incompatible; requires pollinator.
- *Hardiness*.—Hardy in all fruit growing areas of California. Winter chilling requirement is approximately 450 hours at or below 7.2° C.
- *Disease resistance/susceptibility*.—Under close observation in Kern County, Calif., no particular plant/fruit disease resistance/susceptibility has been observed.
- *Insect resistance/susceptibility*.—Under close observation in Kern County, Calif., no particular plant/fruit insect resistance/susceptibility has been observed.

Trunk: (Measurements at approximately 30 cm above soil line on mature tree).

- *Diameter*.—Approximately 10 cm.
- *Texture*.—Medium shaggy, increasing with the age of the tree.
- *Trunk color*.—About Medium Grey 201B, becoming darker with age.

Branches: (Measurements at approximately 90 cm above soil line.).

- *Size*.—Diameter approximately 10 cm.
- *Texture*.—Medium shaggy, increasing with age.
- *Color*.—About Light Grey 201D with highlights of about Medium Greyed-Brown 199B, becoming darker with age.
- *Lenticels*.—Present.
- *Lenticels density*.—Plentiful, about 12/cm$^2$.
- *Lenticels color*.—About Light Grey 201D.
- *Lenticels dimensions*.—Length: approximately 3 mm. Width: approximately 1 mm.

Flowering shoots: (Data taken in September at mid-point of current season growth).

- *Size*.—Average diameter approximately 5 mm.
- *Color*.—Topside: About Dark Greyed-Orange 165A. Underside: About Dark Greyed-Orange 165A.
- *Internode length*.—Approximately 3.5 cm. Midway on flowering shoot.
- *Flowering shoot lenticels*.—Plentiful. Color: About Medium Grey-Brown 199D. Diameter: Approximately 0.3 mm.
- *Flowering shoot vegetative buds*.—Size: Medium, approximately 1.5 mm×2.5 mm. Shape: Conical. Bud shape at apex: Acute. Color: About Dark Brown 200B.
- *Flowering shoot flower buds*.—Shape: Acute. Dimensions: Approximately 1.5 mm×2.8 mm. Color: About Dark Greyed-Orange 177A. Distribution: 2-4 buds, generally on spurs and one year old shoots.
- *Ratio of flowering buds to vegetative buds*.—2-4 flower buds to 1 vegetative bud.
- *Anthocyanin intensity on upper side of shoot*.—Strong.
- *Spur length*.—Medium, usually 10 mm.
- *Position of vegetative bud in relation to shoot*.—Markedly held out.

FOLIAGE

Leaves: (Data taken in September on fully expanded leaves at mid-point of the current season growth).

- *Average length*.—Long; approximately 12.5 cm without petiole.
- *Average width*.—Broad; approximately 4.9 cm.
- *Length/width ratio*.—Moderately elongated, about 2.6:1.
- *Color*.—Upper surface: About Dark Green 139A. Lower surface: About Medium Green 138B.
- *Shape*.—Elliptic.
- *Tip*.—Cuspidate.
- *Base*.—Acuminate.
- *Margin*.—Crenate.
- *Venation*.—Pinnately net veined.
- *Vein color*.—About Light Green 139D with highlights of Medium Greyed-Orange 176C where exposed to sun.
- *Surface texture*.—Smooth upper and lower surfaces.
- *Shape in the cross section*.—Concave.
- *Angle at apex*.—Acute.
- *Profile*.—Up folded.
- *Leaf blade tip*.—Curved downwardly.
- *Undulation of margin*.—Slight.
- *Glossiness of upper side*.—Medium.
- *Density of pubescence of lower side*.—Absent or very sparse.

Petiole:

- *Average length*.—Medium, approximately 10 mm.
- *Average diameter*.—Approximately 2 mm.
- *Color*.—About Light Green 138C with highlights of Medium Greyed-Orange 176C where exposed to sun.

Stipules:

- *Number/leaf bud*.—Usually one.
- *Typical length*.—Approximately 8 mm.
- *Color*.—About Dark Greyed-Orange 166A when dried.
- *Persistence*.—Falls off.

Leaf glands:

- *Average number and arrangement*.—Approximately 1-4, alternating.
- *Form*.—Globose.
- *Diameter*.—Approximately 0.3 mm.
- *Color*.—About Medium Greyed-Yellow 162A becoming Dark Greyed-Orange 166A over time.
- *Positions of nectarines (glands)*.—Predominately on the petiole, also on base of leaf blades.

FLOWERS

General:

- *Time of beginning of flowering*.—Medium for the San Joaquin Valley, Calif.

*Flower blooming period*.—First bloom: Approximately February 19 in Wasco, Calif. Full bloom: Approximately February 23 in Wasco, Calif.
*Location of first bloom*.—Tips of one year old shoots.
*Location of full bloom*.—Central part of the tree canopy.
*Duration of bloom*.—Approximately 10 days.
*Diameter of fully opened flower*.—Medium, approximately 1.8 cm.
*Flower form*.—Showy.

Pedicels:
*Length*.—Long, approximately 12 mm.
*Diameter*.—Approximately 1.2 mm.
*Color*.—About Light Green 138C.
*Pubescence*.—Absent.

Petals:
*Number*.—5.
*Arrangement*.—Slightly overlapping.
*Color*.—About White 155A.
*Length*.—Medium, approximately 8 mm.
*Width*.—Approximately 8 mm.
*Shape*.—Circular.
*Apex shape*.—Rounded.
*Base shape*.—Narrows at point of attachment.
*Surface texture*.—Smooth.
*Undulation of margins*.—Medium.
*Frequency of flowers with double petals*.—None.
*Claw*.—Absent.

Sepals:
*Number*.—5.
*Length*.—Approximately 4 mm.
*Diameter*.—Approximately 3 mm.
*Shape*.—Triangular.
*Color*.—About Light Green 139D.
*Surface texture*.—Smooth.
*Margins*.—Undulating.
*Positioning*.—Adpressed to petals.
*Frequency of flowers with double sepals*.—None.

Stamens:
*Number*.—Usually 32-38, usually 34.
*Average length*.—Variable, ranging from 3 mm to 10 mm.
*Filament color*.—About White 155A.
*Flower pollen color*.—About Light Yellow-Orange 18A.
*Position*.—Perigynous.

Pistil:
*Average length*.—Approximately 3-4 mm.
*Ovary diameter*.—Approximately 2 mm.
*Pubescence*.—Absent.
*Stigma extension in comparison to anthers*.—Usually below.
*Style frequency of supplementary pistils*.—Few.

Receptacle:
*Depth*.—Medium, approximately 4 mm.
*Pubescence of inner surface*.—Absent.
*Pubescence of outer surface*.—Absent.

FRUIT

General: (Description taken near Wasco, Kern County, Calif.).

Ripening:
*Time of beginning of fruit ripening*.—Early season.
*Date of first pick*.—Approximately June 13.
*Date of last pick*.—Approximately June 23.
*Maturity when described*.—Firm.

Size:
*Height*.—Tall, approximately 75 mm.
*Diameter in line with suture plane*.—Approximately 70 mm.
*Diameter perpendicular to suture plane*.—Broad, approximately 70 mm.
*Average weight*.—Very large, approximately 180 gm.

Peduncle:
*Length of stem*.—Short, approximately 7 mm.
*Diameter of stem*.—Approximately 3 mm.
*Color of stem*.—About Light Green 139D.

Shape:
*Viewed from apex*.—Circular.
*Viewed in-line with suture*.—Circular.
*Viewed from side, perpendicular to suture*.—Circular.
*Symmetry*.—Symmetric or slightly asymmetric.
*Shape of base*.—Slightly depressed.
*Shape of apex*.—Slightly pointed.

Fruit stem cavity:
*Depth of stalk cavity*.—Shallow; Approximately 6 mm.
*Width of stalk cavity*.—Medium; Approximately 12 mm.
*Depth of suture*.—Absent.

Fruit skin:
*Thickness*.—Medium.
*Flavor*.—Mildly tart.
*Adherence to flesh*.—Strong.
*Surface texture*.—Smooth.
*Pubescence*.—None.
*Bloom*.—Medium.
*Ground color*.—Not visible.
*Overcolor*.—About Dark Greyed-Purple 187A, becoming fully Black 202A.
*Relative area of overcolor*.—Whole surface.
*Pattern of overcolor*.—Solid.
*Reticulation*.—Slight.
*Tendency to crack*.—Rare.
*Number of lenticels*.—Medium, about 30/cm$^2$.
*Size of lenticels*.—Very small and difficult to see; less than 0.3 mm.

Flesh:
*Ripens*.—Evenly.
*Texture*.—Firm-juicy.
*Flavor*.—Mildly sweet.
*Color*.—About Dark Red 53B.
*Firmness*.—Firm, typically 10 lb pressure to harvest.
*Juice*.—Medium, able to squeeze free juice easily.
*Acidity*.—Medium for plums, 0.50% titratable acidity.
*Sweetness*.—High, about 17 degrees brix at harvest.
*Adherence to stone*.—Semi-free.
*Amount of fiber*.—Low.

Fruit use: Fresh market.

Fruit shipping and keeping quality: Good.

Stone:
*Stone freeness*.—Semi-free.
*Stone size*.—Size: Medium. Length: Approximately 19 mm. Diameter in line with suture plane: Approximately 16 mm. Diameter perpendicular to suture plane: Approximately 6 mm.
*Color*.—About Medium Greyed-Yellow 161B when dried.
*Position of maximum diameter*.—Middle.
*Shape from lateral view*.—Circular.

*Shape from ventral view*.—Narrow elliptic.
*Shape from basal view*.—Narrow elliptic.
*Base shape*.—Nearly straight.
*Apex shape*.—Pointed.
*Stone ridgers*.—Rounded throughout.
*Stone outgrowing keel*.—Well developed.
*Ventrical edge*.—Thin with wing toward middle.
*Dorsal edge*.—Narrow, shallow grooves throughout.
*Fibers*.—Not visible.
*Symmetry in lateral view*.—Moderately asymmetrical.
*Texture of lateral surface*.—Rough.
*Width of stalk-end*.—Narrow.
*Tendency to split*.—Rare.

What is claimed is:

1. A new and distinct variety of plum tree as herein described and illustrated.

* * * * *

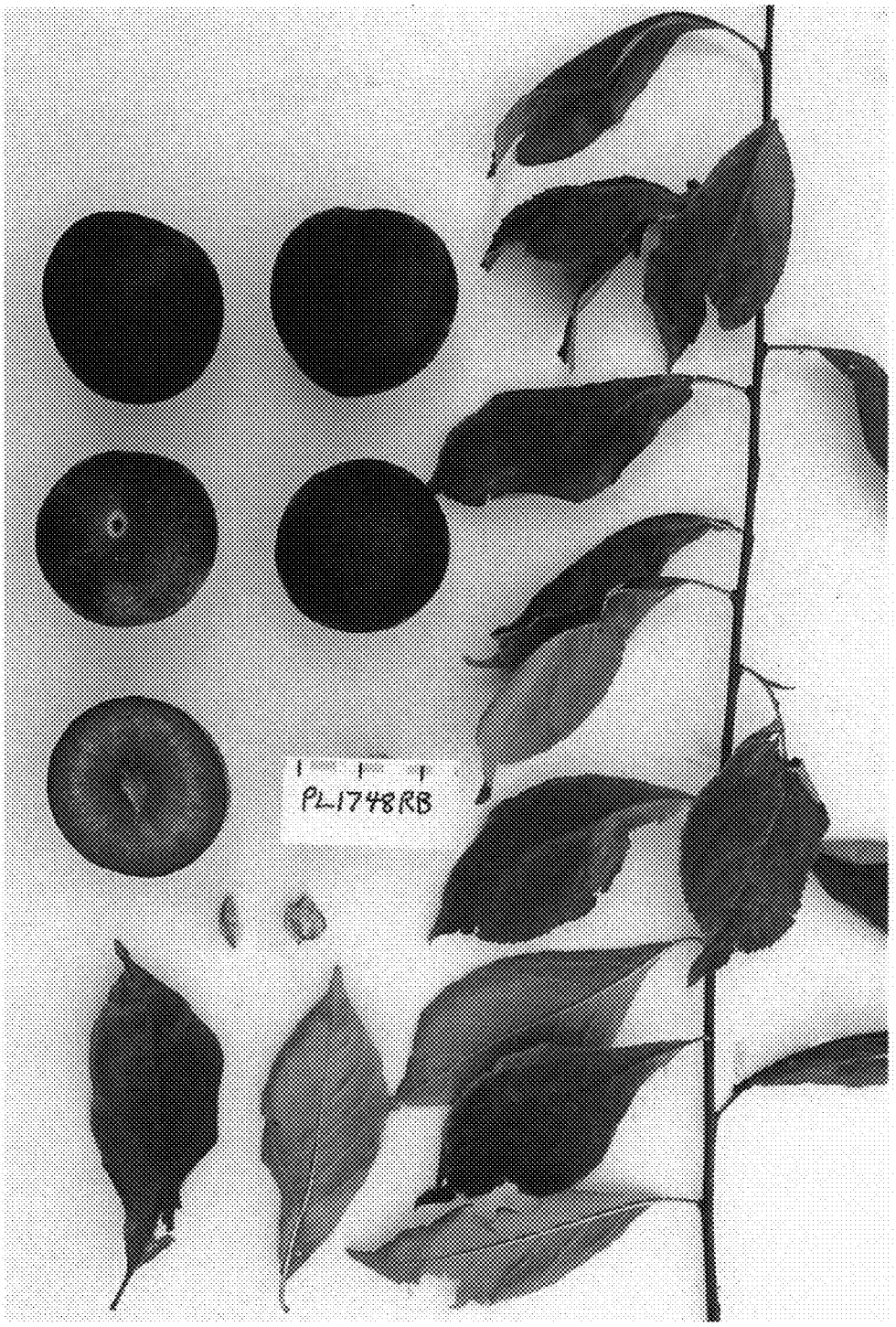
PL1748RB